(12) United States Patent
Cui et al.

(10) Patent No.: US 11,993,664 B2
(45) Date of Patent: May 28, 2024

(54) CRYSTALLINE FORM OF COMPOUND AND USES THEREOF IN MEDICINE

(71) Applicant: WATERSTONE PHARMACEUTICALS(WUHAN) CO., LTD., Wuhan (CN)

(72) Inventors: Jian Cui, Wuhan (CN); Yao Yu, Wuhan (CN); Minglong Hu, Wuhan (CN)

(73) Assignee: WATERSTONE PHARMACEUTICALS(WUHAN) CO., LTD., Wuhan (CN)

( * ) Notice: Subject to any disclaimer, the term of this patent is extended or adjusted under 35 U.S.C. 154(b) by 647 days.

(21) Appl. No.: 17/270,197

(22) PCT Filed: Aug. 22, 2019

(86) PCT No.: PCT/CN2019/101920
§ 371 (c)(1),
(2) Date: Feb. 22, 2021

(87) PCT Pub. No.: WO2020/038426
PCT Pub. Date: Feb. 27, 2020

(65) Prior Publication Data
US 2021/0324008 A1 Oct. 21, 2021

(30) Foreign Application Priority Data
Aug. 22, 2018 (WO) ............... PCT/CN2018/101674

(51) Int. Cl.
| | | |
|---|---|---|
| C07K 7/00 | (2006.01) | |
| A61K 31/4178 | (2006.01) | |
| A61K 31/439 | (2006.01) | |
| A61K 31/7056 | (2006.01) | |
| A61K 31/7072 | (2006.01) | |
| A61K 38/13 | (2006.01) | |
| A61K 38/21 | (2006.01) | |
| A61P 31/14 | (2006.01) | |
| C07K 7/64 | (2006.01) | |

(52) U.S. Cl.
CPC .......... *C07K 7/645* (2013.01); *A61K 31/4178* (2013.01); *A61K 31/439* (2013.01); *A61K 31/7056* (2013.01); *A61K 31/7072* (2013.01); *A61K 38/13* (2013.01); *A61K 38/212* (2013.01); *A61P 31/14* (2018.01); *C07B 2200/13* (2013.01)

(58) Field of Classification Search
CPC .. C07K 7/645; A61K 31/4178; A61K 31/439; A61K 31/7056; A61K 31/7072; A61K 38/13; A61K 38/212; A61P 31/14; C07B 2200/13
See application file for complete search history.

(56) References Cited

U.S. PATENT DOCUMENTS

| | | |
|---|---|---|
| 5,994,299 A | 11/1999 | Barriere et al. |
| 2010/0173838 A1 | 7/2010 | Viskov |
| 2016/0015632 A1 | 1/2016 | Gore et al. |

FOREIGN PATENT DOCUMENTS

| | | |
|---|---|---|
| EP | 0414632 A2 | 2/1991 |
| JP | 2014532071 A | 12/2014 |
| JP | 2016-504314 A | 2/2016 |
| JP | 2021509987 A | 4/2021 |
| WO | 2006039668 A2 | 4/2006 |
| WO | 2007041632 A2 | 4/2007 |
| WO | 2011072370 A1 | 6/2011 |
| WO | 2017200984 A1 | 11/2017 |

OTHER PUBLICATIONS

McPherson and Gavira (Acta Cryst. (2014). F70, 2-20.*
Fu et al. (Development of a cyclosporin A derivative with excellent anti-hepatitis C virus potency, Bioorganic & Medicinal Chemistry. 26(4), 2018.*
International Search Report issued in International Application No. PCT/CN2018/101674 dated May 20, 2019 (14 pages).
International Search Report issued in International Application No. PCT/CN2019/101920 dated Oct. 30, 2019 (8 pages).
Office Action Issued in Corresponding Japanese Application No. 2021-509987, dated Mar. 8, 2022, 11 pages.
Extended European Search Report issued in corresponding EP Application No. 19851016.6 dated May 25, 2022 (9 pages).
Hopkins, S. et al. "The Cyclophilin Inhibitor SCY-635 Disrupts Hepatitis C Virus NS5ACyclophilin A Complexes" Antimicrobial Agents and Chemotherapy, Jul. 2012, vol. 56, No. 7, pp. 3888-3897 (12 pages).
Alvarez, A. J. et al. "Crystallization of Cyclosporine in a Multistage Continuous MSMPR Crystallizer" ACS Publications, Crystal Growth Des. 2011, 11, pp. 4392-4400 (10 pages).
Notice of Reasons for Refusal issued in Japanese Application No. 2022-202703 mailed on Dec. 12, 2023 (11 pages).

* cited by examiner

*Primary Examiner* — Jeanette M Lieb
(74) *Attorney, Agent, or Firm* — Osha Bergman Watanabe & Burton LLP

(57) ABSTRACT

A crystalline form A of the compound having formula (I) and uses thereof in medicine are described. Specifically, it relates to crystalline form A and pharmaceutically compositions thereof. Furthermore, it relates to the uses of crystalline form A disclosed herein and pharmaceutically compositions thereof disclosed herein in the manufacture of a medicament, especially in the manufacture of a medicament for preventing, managing, treating or lessening hepatitis C virus (HCV) infection.

9 Claims, 5 Drawing Sheets

CRYSTALLINE FORM OF COMPOUND AND USES THEREOF IN MEDICINE

CROSS-REFERENCE TO RELATED APPLICATION

The application is a U.S. national phase application based on the PCT Application No. PCT/CN2019/101920 filed on Aug. 22, 2019, which claims a priority to and benefits of PCT Application No. PCT/CN2018/101674, filed with the State Intellectual Property Office of P. R. China on Aug. 22, 2018, the entire contents of which are incorporated herein by reference.

FIELD

The present invention belongs to the field of medicine. Specifically, it relates to a crystalline form A of (3 S,6S,9S, 12R,15S,18S,21S,24S,27R,30S,33S)-27-((2-(dimethyl-amino)ethyl)thio)-30-ethyl-33-((1R,2R,E)-1-hydroxy-2-methylhex-4-en-1-yl)-24-(2-hydroxy-2-methylpropyl)-6,9,18-triisobutyl-3,21-diisopropyl-1,4,7,10,12,15,19,25,28-nonamethyl-1,4,7,10,13,16,19,22,25,28,31-undecaazacyc lotritriacontan-2,5,8,11,14,17,20,23,26,29,32-undecaone and pharmaceutically composition thereof. Furthermore, it relates to the uses of the crystalline form A and pharmaceutically compositions thereof in the manufacture of a medicament, especially in the manufacture of a medicament for preventing, managing, treating or lessening hepatitis C virus (HCV) infection.

BACKGROUND

Hepatitis C virus (HCV) is a member of the Flaviviridae family, which comprises three distinct genera, including the flaviviruses (such as yellow fever virus, dengue virus, West Nile virus, and Japanese encephalitis virus), the pestiviruses (bovine viral diarrhea virus and classical swine fever virus), and the hepaciviruses (of which HCV is the only member). Chronic infection with HCV now represents a major global health problem, with approximately 170 million people worldwide being infected.

SCY-635 (the compound having formula (I)) is an orally bioavailable, novel analog of cyclosporine A (CsA) that is a reversible, competitive, active site-directed inhibitor of cyclophilin A and inhibits peptidyl prolyl isomerase (PPIase) catalytic activity at low nanomolar (nM) concentrations. SCY-635 has been investigated for the treatment of Chronic Hepatitis C and Hepatitis C Infection.

Different solid forms of a pharmaceutically active ingredient may have different properties. The change of properties of different solid forms can provide improved formulations, such as easily synthesis or managing, improvement of dissolution rate or stability and shelf life. The final dosage form can also be improved due to changes in properties caused by different solid forms, for example if such changes can increase exposure, bioavailability or prolong half-life. Different solid forms of the pharmaceutically active ingredient can also produce polycrystalline or other crystalline forms, thereby providing more opportunities to assess the property changes of a solid active pharmaceutical ingredient.

SUMMARY OF THE INVENTION

In order to find a solid form having a better druggability, the inventors have obtained the crystalline form A of the compound having formula (I) through many experimental studies. The preparation purity of the product has obviously improved, and the physical properties are more favorable for the formulation. The preparations of crystalline form A of the compound having formula (I), properties of drug metabolism and the physicochemical properties thereof, and the like, have been researched, and it has been found that the crystal form A of the compound having formula (I) has better solubility, stability and pharmacokinetic properties, and the like.

The present invention relates to free base crystalline form A of (3 S,6S,9S,12R,15S,18S,21S,24S,27R,30S,33S)-27-((2-(dimethylamino)ethyl)thio)-30-ethyl-33-((1R,2R,E)-1-hydroxy-2-methylhex-4-en-1-yl)-24-(2-hydroxy-2-methyl-propyl)-6,9,18-triisobutyl-3,21-diisopropyl-1,4,7,10,12,15,19,25,28-nonamethyl-1,4,7,10,13,16,19,22,25,28,31-undecaazacyc lotritriacontan-2,5,8,11,14,17,20,23,26,29,32-undecaone (I), and pharmaceutically compositions thereof. Furthermore, it relates to the uses of the crystalline form A thereof, and pharmaceutical composition thereof in the manufacture of a medicament, especially in the manufacture of a medicament for preventing, managing, treating or lessening HCV infection.

In one aspect, provided herein is the crystalline form A of the compound having formula (I):

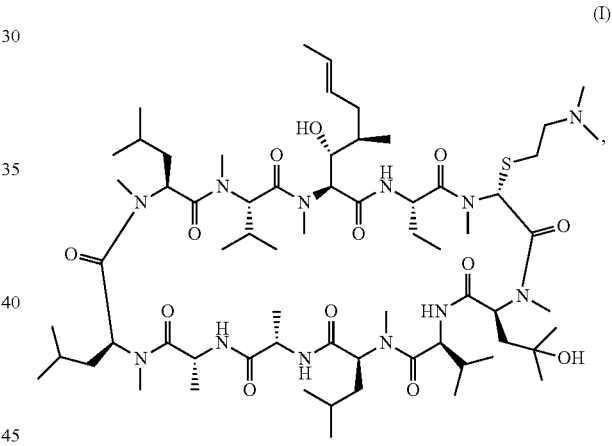

(I)

wherein the crystalline form A exhibits the following characteristic X-ray powder diffraction peaks expressed in degrees 2θ at 8.66±0.2°, 9.64±0.2°, 10.36±0.2°, 11.20±0.2°, 18.39±0.2°.

In some embodiments, the crystalline form A disclosed herein exhibits the following characteristic X-ray powder diffraction peaks expressed in degrees 2θ at 6.08±0.2°, 8.66±0.2°, 9.64±0.2°, 10.36±0.2°, 11.20±0.2°, 13.00±0.2°, 14.14±0.2°, 14.90±0.2°, 18.39±0.2°, 20.40±0.2°, 22.04±0.2°.

In some embodiments, the crystalline form A disclosed herein exhibits the following characteristic X-ray powder diffraction peaks expressed in degrees 2θ at 6.08±0.2°, 8.66±0.2°, 9.64±0.2°, 10.36±0.2°, 11.20±0.2°, 12.58±0.2°, 13.00±0.2°, 13.58±0.2°, 14.14±0.2°, 14.90±0.2°, 15.36±0.2°, 15.98±0.2°, 16.71±0.2°, 17.69±0.2°, 18.39±0.2°, 18.78±0.2°, 19.38±0.2°, 20.40±0.2°, 21.71±0.2°, 22.04±0.2°, 22.49±0.2°, 23.20±0.2°, 23.88±0.2°, 24.99±0.2°, 25.82±0.2°, 26.77±0.2°, 27.61±0.2°, 28.43±0.2°, 29.62±0.2°, 31.36±0.2°.

In some embodiments, the crystalline form A disclosed herein has an X-ray powder diffraction pattern substantially the same as shown in FIG. 1.

In some embodiments, the crystalline form A disclosed herein has a differential scanning calorimetry thermogram comprising an endothermic peak at 143.8° C.±3° C. and 172.6° C.±3° C.

In some embodiments, the crystalline form A disclosed herein has a differential scanning calorimetry thermogram substantially the same as shown in FIG. 2.

In another aspect, provided herein is a pharmaceutical composition comprising the crystalline form A disclosed herein.

In some embodiments, the pharmaceutical composition disclosed herein further comprises a pharmaceutically acceptable excipient, or a combination of the excipients.

In some embodiments, the pharmaceutical composition disclosed herein further comprises other anti-HCV drug.

In some embodiments, the pharmaceutical composition disclosed herein, wherein the other anti-HCV drug is Ledipasvir/sofosbuvir, Sofosbuvir, Ribavirin, Peginterferon alfa-2a or Daclatasvir.

In one aspect, provided herein is use of the crystalline form A of the compound having formula (I) or the pharmaceutical composition disclosed herein in the manufacture of a medicament for preventing, treating or lessening a disorder or disease caused by a virus infection in a patient.

In some embodiments, the use disclosed herein, wherein the virus infection is hepatitis C infection.

In another aspect, provided herein is the crystalline form A of the compound having formula (I) or the pharmaceutical composition disclosed herein for use in preventing, treating or lessening a disorder or disease caused by a virus infection in a patient.

In some embodiments, the crystalline form A or the pharmaceutical composition disclosed herein, wherein the virus infection is hepatitis C infection.

In one aspect, provided herein is a method of preventing, treating or lessening a disorder or disease caused by a virus infection in a patient comprising administering to the patient a therapeutically effective amount of the crystalline form A of the compound having formula (I) or the pharmaceutical composition disclosed herein.

In some embodiments, the method disclosed herein, wherein the virus infection is hepatitis C infection.

DETAILED DESCRIPTION OF THE INVENTION

The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

In the invention, the crystalline form A of the compound having formula (I) may contain solvent. In some embodiments, the solvent contained herein contributes to the internal stability of the crystalline form A of the compound having formula (I). Common solvents include, water, ethanol, methanol, isopropanol, acetone, isopropyl ether, ethyl ether, isopropyl acetate, n-heptane, tetrahydrofuran, dichloromethane, ethyl acetate, etc. The above-mentioned crystalline form having a certain amount of water or other solvent has the characteristics of the crystalline form A of the compound represented by formula (I) according to the present invention, it is intended to be included within the scope of the present invention.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety. Although many methods and materials similar or equivalent to those described herein could be used in the practice or test of the present invention, the preferred methods, equipment and materials are described in the invention.

Definitions and General Terminology

The term "comprise" is an open expression, it means comprising the contents disclosed herein, but don't exclude other contents.

As described herein, "room temperature" refers to a temperature from about 10° C. to about 40° C. In some embodiments, "room temperature" refers to a temperature from about 20° C. to about 30° C.; In other embodiments, "room temperature" refers to a temperature from about 25° C. to about 30° C.

The term as used herein, "pharmaceutically acceptable" means a substance is acceptable from the standpoint of toxicology for pharmaceutical applications and does not adversely interact with active ingredients.

Polymorphic substance can be detected, identified, classified and characterized by known technologies, including but not limited to: differential scanning calorimetry (DSC), thermogravimetric analysis (TGA), X-ray powder diffraction (XRPD), X-ray single crystal diffraction, vibrational spectroscopy, solution calorimetry, solid state nuclear magnetic resonance (SSNMR), Fourier transform infrared spectroscopy (FT-IR spectrum), Raman spectroscopy, hot stage optical microscopy, scanning electron microscopy (SEM), electron crystallography, and quantitative analysis, particle size analysis (PSA), surface area analysis, solubility and dissolution rates. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

As used herein to refer to the spectra or data presented in graphical form (e.g., XRPD), and unless otherwise indicated, the term "peak" refers to a peak or other special feature that one skilled in the art would recognize as not attributable to background noise.

"XRPD" refers to X-ray powder diffraction.

Some informations such as change in crystalline form, crystallinity, crystal structure state, etc., can be obtained through detection of X-ray powder diffraction (XRPD) which is a common method used for identifying crystalline form. The term "X-ray powder diffraction pattern" or "XRPD pattern" refers to the experimentally observed diffractogram or parameters derived therefrom. The X-ray powder diffraction (XRPD) is characterized by the peak position (abscissa) and the peak intensity (ordinate). The peak position of XRPD pattern mainly depends on the crystal structure, which is relatively insensitive to experimental details, and the relative peak height depends on many factors related to sample preparation and the geometry of the instrument. Thus, in some embodiments, the crystalline form disclosed herein is characterized by an X-ray powder diffraction pattern having some peaks in certain positions, which is substantially the same as the XRPD pattern provided in appended figures of the present invention. Meanwhile, the measurement of 2θ in XRPD pattern could have some experimental error, for example the measurements of 2θ in XRPD pattern could be different because of different instruments and different samples. Therefore, the value of 2θ is not absolute. According to the state of the instrument for the experiment disclosed herein, the error margin in 2θ of the diffraction peak is ±0.1°, ±0.2°, ±0.3°, ±0.4° or ±0.5°; in some embodiments, the error margin in 2θ of the diffraction peak is ±0.2°.

The term "2 theta value" or "2θ" refers to the peak position in degrees based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ). It should be understood that reference herein to specific 2θ values for a specific solid form is intended to mean the 2θ values (in degrees) as measured using the X-ray diffraction experimental conditions as described herein.

As used herein, the value of 2θ described in an X-ray powder diffraction pattern is recorded in degree (°).

As used herein, the term "relative intensity" refers to the intensity of a peak with respect to the intensity of the strongest peak in the X-ray powder diffraction (XRPD) pattern which is regarded as 100%.

Differential scanning calorimetry (DSC) is a technology used for measuring the energy difference between a sample and a inert reference compound (usually α-$Al_2O_3$) as a function of temperature, which is performed through constant heating or cooling under program control. The melting peak height of DSC thermogram depends on many factors related to sample preparation and the geometry of the instrument, and the peak position is relatively insensitive to experimental details. Thus, in some embodiments, the crystalline form disclosed herein is characterized by a DSC thermogram having some peaks in certain positions, which is substantially the same as the DSC thermogram provided in appended figures of the present invention. Meanwhile, the measurement of DSC thermogram could have some experimental error, for example the measurements of peak position and peak value in DSC thermogram could be different because of different instruments and different samples. Therefore, the numerical value of peak position and peak value of endothermic peak in DSC thermogram is not absolute. According to the state of the instrument for the experiment disclosed herein, the error margin in the melting peaks is ±1° C., ±2° C., ±3° C., ±4° C. or ±5° C. In some embodiments, the error margin in the melting peaks is ±3° C. Differential scanning calorimetry (DSC) also is used for detection and analysis whether there is crystal transformation or mixed grain phenomenon in crystalline form.

Solids having same chemical composition usually form polymorphs, or called variant, having different crystal structures under different thermodynamic conditions, this phenomenon is called polymorphism or polyphase. When conditions of temperature and pressure change, there will be a change between variants, which is called crystal transition. The property of crystalline forms changed largely such as mechanics, electrics, magnetics because of crystal transition. The crystal transition process could be observed in differential scanning calorimetry (DSC) thermogram when the transition temperature within a measurable range, which is characterized by the DSC thermogram having a exothermic peak reflecting this transformation and two or more endothermic peaks which respectively are characteristic endothermic peaks of different crystalline forms before and after the transformation.

Thermogravimetric analysis (TGA) is a technology used for measuring the quality change of a substance which varies with temperature of a substance under program control, which can apply to detecting the process of the solvent loss in the crystal, sublimation and dissociation of the sample, and the crystal water and the crystal solvent contained in crystal may be speculated through analysis of the detection results. The measurement of quality change described in TGA curve depends on many factors such as sample preparation and instrument geometry, etc., which could be different because of different instruments and different samples. According to the state of the instrument for the experiment disclosed herein, the error margin of the quality change is ±0.1%.

"Amorphism" or "amorphous form" refers to substance forming by particle (such as molecule, atom, ion) arranged in no periodic in three-dimensional space, which is characterized by a diffused X-ray powder diffraction pattern with no sharp peaks. Amorphism is a special physical form of solid substance, the ordered structural characteristics in a part of amorphous substance imply there are innumerable links between amorphous substance and crystal substance. Amorphous form of a substance can be obtained by a number of methods as known in the art. These methods include, but are not limited to, rapid freezing method, anti-solvent flocculence, ball-milling method, spray drying method, freeze-drying method, wet granulating method and solid dispersion technique, and the like.

The term "solvent", as used herein, means a substance, typically a liquid, that is capable of completely or partially dissolving another substance, typically a solid. Solvents for the practice of the invention include, but are not limited to, water, acetic acid, ethyl ether, isopropyl ether, petroleum ether, isopropyl acetate, methyl tert-butyl ether, n-heptane, acetone, acetonitrile, benzene, chloroform, tetrachloromethane, dichloromethane, dimethyl sulfoxide, 1,4-dioxane, ethanol, ethyl acetate, n-butanol, tert-butanol, N,N-dimethylacetamide, N,N-dimethylformamide, formamide, formic acid, hexane, isopropanol, methanol, methyl ethyl ketone, 1-methyl-2-pyrrolidone, mesitylene, nitromethane, polyethylene glycol, n-propanol, 2-acetone, pyridine, tetrahydrofuran, toluene, xylene, mixtures thereof, etc.

The term "anti-solvent" refers to a fluid which promotes precipitation from the solvent of the product (or a precursor for the product). The anti-solvent may comprise a cold gas, or a fluid promoting the precipitation via a chemical reaction, or a fluid which decreases the solubility of the product in the solvent; it may be the same liquid as the solvent but at a different temperature or it may be a different liquid from the solvent.

The term "solvate", as used herein, means having on a surface, in a lattice or on a surface and in a lattice, solvents for the practice of the invention include, but are not limited to, water, acetic acid, acetone, acetonitrile, benzene, chloroform, tetrachloromethane, dichloromethane, dimethyl sulfoxide, 1,4-dioxane, ethanol, ethyl acetate, butanol, tert-butanol, N,N-dimethylacetamide, N,N-dimethylformamide, formamide, formic acid, heptane, hexane, isopropanol, methanol, methyl ethyl ketone, 1-methyl-2-pyrrolidone, mesitylene, nitromethane, polyethylene glycol, propanol, 2-acetone, pyridine, tetrahydrofuran, toluene, xylene, mixtures thereof, etc. A specific example of a solvate is a hydrate, wherein the solvent on the surface, in the lattice or on the surface and in the lattice, is water. Hydrates may or may not have solvents other than water on the surface, in the lattice or on the surface and in the lattice of a substance.

The term "equivalent" or "eq", is the equivalent amount of other raw materials needed according to the chemical reaction equivalent relationship, wherein the basic raw material is used as the base (1 equivalent) in each step.

Crystalline form or amorphism can be identified through multiple technological means, such as X-ray powder diffraction (XRPD), infrared spectroscopy (IR), melting point, differential scanning calorimetry (DSC), thermogravimetry analysis (TGA), nuclear magnetic resonance, raman spectroscopy, single-crystal X-ray diffraction, solution calorimetry, scanning electron microscope (SEM), quantitative analysis, solubility, dissolution velocity, etc.

As used herein, term "substantially the same as shown in a figure" refers to an X-ray powder diffraction (XRPD) pattern, or a differential scanning calorimetry (DSC) thermogram, or a Raman spectrogram, or a Fourier transform infrared spectrogram having at least 50%, at least 60%, at least 70%, at least 80%, at least 90%, at least 95%, or at least 99% of the peaks shown in the figure.

As used herein, when referring to a spectrum and/or to data presented in a graph, the term "peak" refers to a feature that one skilled in the art would recognize as not attributable to background noise.

As used herein, a crystalline form that is "substantially pure" refers to a crystalline form that is substantially free of one or more other crystalline forms, i.e., the crystalline form has a purity of at least about 80%, at least about 85%, at least about 90%, at least about 93%, at least about 95%, at least about 98%, at least about 99%, at least about 99.5%, at least about 99.6%, at least about 99.7%, at least about 99.8%, or at least about 99.9%; or the crystalline form has less than 20%, less than 10%, less than 5%, less than 3%, less than 1%, less than 0.5%, less than 0.1%, or less than 0.01% of the one or more other crystalline forms, based on the total volume or weight of the crystalline form and the one or more other crystalline forms.

As used herein, a crystalline form that is "substantially free" of one or more other crystalline forms refers to a crystalline form containing less than 20%, less than 10%, less than 5%, less than 4%, less than 3%, less than 2%, less than 1%, less than 0.5%, less than 0.1%, or less than 0.01% of the one or more other crystalline forms, based on the total volume or weight of crystalline form and the one or more other crystalline forms.

As used herein, all numbers disclosed herein are approximate values, regardless whether the word "about" is used in connection therewith, which means within 10%, suitably within 5% and particularly within 1% of a given value or range. Alternatively, the term "about" means within an acceptable standard error range of the mean, when considered by one of the ordinary skill in the art. Therefore, whenever a number having a value N is disclosed, any number having the value N+/−1%, N+/−2%, N+/−3%, N+/−5%, N+/−7%, N+/−8% or N+/−10% is specifically disclosed, wherein "+/−" refers to plus or minus.

As used herein, "patient" refers to a human (including adults and children) or other animal. In one embodiment, "patient" refers to a human.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment, "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As described above, the pharmaceutically acceptable compositions disclosed herein further comprise a pharmaceutically acceptable excipient, which, as used herein, includes any and all solvents, solid excipients, diluent, adhesives, disintegrant or other liquid vehicle, dispersion, flavoring agents or suspension aids, surface active agents, isotonic agents, thickening or emulsifying agents, preservatives, solid binders, glidants, lubricants and the like, as suited to the particular dosage form desired. As the following described: Troy et al., *Remington: The Science and Practice of Pharmacy,* 21st ed., 2005, Lippincott Williams & Wilkins, Philadelphia, and Swarbrick et al., *Encyclopedia of Pharmaceutical Technology,* eds. 1988-1999, Marcel Dekker, New York, both of which are herein incorporated by reference in their entireties, discloses various excipients used in formulating pharmaceutically acceptable compositions and known techniques for the preparation thereof. Except insofar as any conventional excipients incompatible with the compounds disclosed herein, such as by producing any undesirable biological effect or otherwise interacting in a deleterious manner with any other components of the pharmaceutically acceptable composition, its use is contemplated to be within the scope of this invention.

Some non-limiting examples of materials which can serve as pharmaceutically acceptable excipients include ion exchangers; aluminium; aluminum stearate; lecithin; serum proteins such as human serum albumin; buffer substances such as phosphates; glycine; sorbic acid; potassium sorbate; partial glyceride mixtures of saturated vegetable fatty acids; water; salts or electrolytes such as protamine sulfate, disodium hydrogen phosphate, potassium hydrogen phosphate, sodium chloride and zinc salts; colloidal silica; magnesium trisilicate; polyvinyl pyrrolidone; polyacrylates; waxes; polyethylene-polyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The crystalline form or pharmaceutical composition disclosed herein may be administered in any of the following routes: orally, inhaled by spray, locally, rectally, nasally, vaginally, parenterally such as subcutaneous, intravenous, intramuscular, intraperitoneal, intrathecal, intraventricular, intrasternal, or intracranial injection or infusion, or administered with the aid of an explanted reservoir. Administration routes by orally, intramuscular, intraperitoneal or intravenous injection are preferred.

The crystalline form or pharmaceutically acceptable composition thereof may be administered in a unit dosage form. The dosage form may be in a liquid form, or a solid form. The liquid form includes true solutions, colloids, particulates, suspensions. Other dosage forms include tablets, capsules, dropping pills, aerosols, pills, powders, solutions, suspensions, emulsions, granules, suppositories, freeze-dried powder injection, and the like.

Oral tablets and capsules may comprise excipients, e.g., binders, such as syrup, arabic gum, sorbitol, tragacanth or polyvinylpyrrolidone; fillers, such as lactose, sucrose, corn starch, calcium phosphate, sorbitol, glycine; lubricants such as magnesium stearate, talc, polyethylene glycol, silica; disintegrating agents, such as potato starch; or acceptable moisturizing agents such as sodium lauryl sulfate. Tablets may be coated by using known methods in pharmaceutics.

Oral solution may be made as a suspension of water and oil, a solution, an emulsion, syrup or an elixir, or made as a dried product to which water or other suitable medium is added before use. This liquid preparation may comprise conventional additives, e.g., suspending agents, sorbitol, cellulose methyl ether, glucose syrup, gel, hydroxyethyl cellulose, carboxymethyl cellulose, aluminum stearate gel, hydrogenated edible greases; emulsifying agents such as lecithin, sorbitan monoleate, arabic gum; or non-aqueous carriers (possibly including edible oil), such as almond oil, grease such as glycerin, ethylene glycol, or ethanol; antiseptics such as methyl or propyl p-hydroxybenzoate, sorbic acid. If desired, a flavoring agent or a colorant may be added.

Suppositories may comprise a conventional suppository base, such as cocoa butter or other glyceride.

For parenteral administration, the liquid dosage form is usually made from the compound and a sterilized carrier. The preferred carrier is water. According to the difference of selected carrier and drug concentration, the compound can be either dissolved in the carrier or made into a supernatant solution. When being made into a solution for injection, the compound is firstly dissolved in water, and then filtered and sterilized before being packaged into a sealed bottle or an ampoule.

For application topically to the skin, the compound disclosed herein may be made into a suitable form of ointments, lotions or creams, wherein the active ingredient is suspended or dissolved in one or more carrier(s). Wherein carriers used for an ointment preparation include, but are not limited to: mineral oil, liquid vaseline, white vaseline, propylene glycol, polyoxyethylene, polyoxypropylene, emulsified wax and water; carriers used for a lotion and a cream include, but are not limited to: mineral oil, sorbitan monostearate, Tween 60, cetyl ester wax, hexadecylene aromatic alcohol, 2-octyl dodecanol, benzyl alcohol and water.

The total administrated dose of the active compound disclosed herein is varied according to the kind and the body weight of treatment objects, the nature and the severity of diseases, the type of preparations and the method of administration of drugs, and administration period or time interval.

DESCRIPTION OF THE PREFERRED EMBODIMENTS

Figure 1:
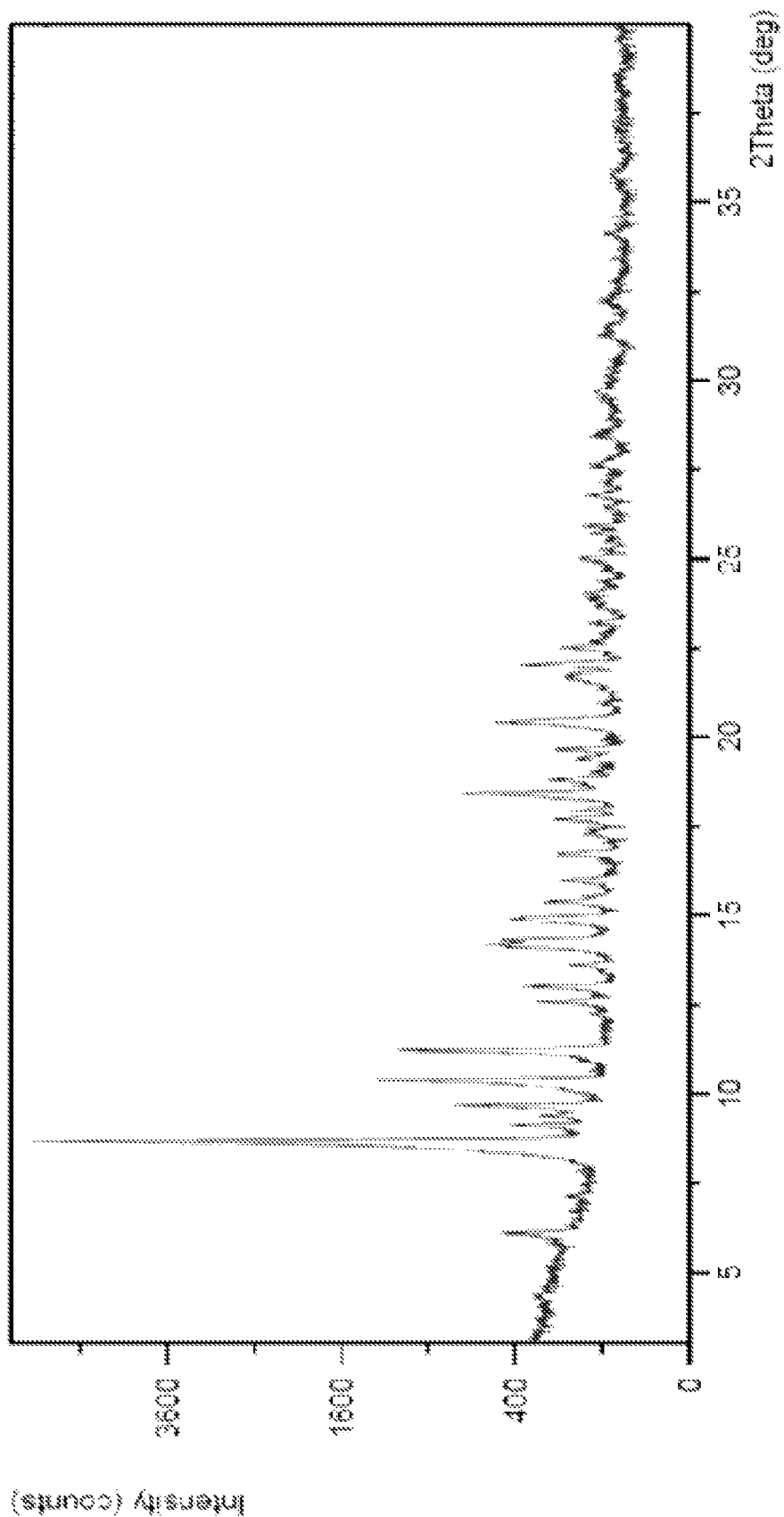
FIG. 1 provides an XRPD pattern of crystalline form A of the compound having formula (I).

The embodiment of the present invention is described in detail, and an example of the embodiment is shown in the drawing. The embodiments described below by reference to the drawings are illustrative and are intended to be used to interpret the present invention and cannot be understood as a limitation to the present invention.

Crystalline forms may be prepared by a variety of methods, including but not limited to, for example, crystallization or recrystallization from a suitable solvent mixture, sublimation, solid state transformation from another phase, crystallization from a supercritical fluid, and jet spraying. Techniques for crystallization or recrystallization of crystalline forms from a solvent mixture include but are not limited to, for example, evaporation of the solvent, decreasing the temperature of the solvent mixture, crystal seeding a supersaturated solvent mixture of the molecule and/or salt, freeze drying the solvent mixture, and addition of anti-solvents (counter-solvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, 2nd Edition, SSU, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an anti-solvent to decrease the solubility of the compound in the solution and to afford the formation of crystals. An anti-solvent is a solvent in which the compound has low solubility.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "*Programmed Cooling Batch Crystallizers*", J. W. Mullin and J.

Nyvlt, *Chemical Engineering Science,* 1971, 26, 369-377. In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity of the desired crystal form (i.e., changing to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, including but not limited to, differential scanning calorimetry (DSC), X-Ray powder diffraction (XRPD), thermogravimetric analysis (TGA), to assure formation of the preferred crystalline form of the product. The resulting crystalline form is typically produced in an amount of greater than about 70 weight percent isolated yield, preferably greater than 90 weight percent isolated yield, based on the weight of the compound originally employed in the crystallization procedure. The product may be co-milled or passed through a mesh screen to delump, if necessary.

The features and advantages of the present invention will become apparent to those of ordinary skilled in the art upon reading the following detailed description. It should be understood that certain features of the invention, which are, for clarity, described in the context of separate embodiments, can also be provided in combination in a single embodiment. Conversely, various features of the invention which are, for brevity, described in the context of a single embodiment, can also be provided in any suitable subcombination. The following examples disclosed herein are presented to further describe the invention. However, these examples should not be used to limit the scope or spirit of the invention to the specific steps described therein.

In the examples described below, unless otherwise indicated all temperatures are set forth in degrees Celsius (° C.).

Reagents were purchased from commercial suppliers such as Aldrich Chemical Company, Sinopharm Chemical Reagent Co., Ltd and were used without further purification unless otherwise indicated. Common solvents were purchased from commercial suppliers such as Wuhan Zhong-Tian Chemical Factory.

$^1$H NMR spectra were recorded by a Bruker Avance 400 spectrometer or Bruker Avance III HD 600 spectrometer, using CDCl$_3$, DMSO-d$_6$, CD$_3$OD or acetone-d$_6$ (reported in ppm) as solvent, and using TMS (0 ppm) or chloroform (7.26 ppm) as the reference standard. When peak multiplicities are reported, the following abbreviations are used: s (singlet), s,s (singlet, singlet), d (doublet), t (triplet), m (multiplet), br (broadened), dd (doublet of doublets), ddd (doublet of doublet of doublets), dt (doublet of triplets), ddt (doublet of doublet of triplets), td (triplet of doublets), br.s (broadened singlet). Coupling constants J, when given, were reported in Hertz (Hz).

The abbreviations for solvents used are listed in Table 1.

TABLE 1

Abbreviations of solvents

| Abbreviation | Solvent | Abbreviation | Solvent |
|---|---|---|---|
| EtOH | Ethanol | THF | Tetrahydrofuran |
| ACN | Acetonitrile | EtOAc | Ethyl acetate |

TABLE 1-continued

Abbreviations of solvents

| Abbreviation | Solvent | Abbreviation | Solvent |
|---|---|---|---|
| IPAc | Isopropyl acetate | MIBK | Methylisobutylketone |

The crystalline form prepared in the invention was identified by the following methods:

For XRPD analysis, a PANalytical Empyrean X-ray powder diffractometer was used. The parameters used are listed in Table 2.

TABLE 2

Parameters for XRPD test

| Parameter | Value |
|---|---|
| X-Ray wavelength | Cu, kα, Kα1 (Å): 1.540598, Kα2 (Å): 1.544426 |
| | Kα2/Kα1 intensity ratio: 0.50 |
| X-Ray tube setting | 45 kV, 40 mA |
| Divergence slit | Automatic |
| Scan mode | Continuous |
| Scan range (° 2TH) | 3°-40° |
| Step size (° 2TH) | 0.013 |
| Scan speed (°/min) | About 8 |

TGA data were collected using a TA Q500/Q5000 TGA from TA Instruments. DSC was performed using a TA Q200/Q2000 DSC from TA Instruments. Detailed parameters used are listed in Table 3.

TABLE 3

Parameters for TGA and DSC test

| Parameters | TGA | DSC |
|---|---|---|
| Method | Ramp | Ramp |
| Sample pan | Platinum, open | Aluminum, crimped |
| Temperature | RT-300° C. | 25-300° C. |
| Heating rate | 10° C./min | 10° C./min |
| Purge gas | N$_2$ | N$_2$ |

Agilent 1100 HPLC was utilized to measure solubility and purity, method listed in Table 4 and Table 5, respectively.

TABLE 4

HPLC method for solubility test

| HPLC | Agilent 1100 with DAD detector |
|---|---|
| Column | Waters Xbridge C18, 150 × 4.6 mm 5 μm |
| Mobile phase | A: 0.1% TFA in H$_2$O |
| | B: 0.1% TFA in acetonitrile |

| Gradient table | Time (min) | % B |
|---|---|---|
| | 0.0 | 5 |
| | 6.0 | 90 |
| | 7.0 | 90 |
| | 7.1 | 5 |
| | 10.0 | 5 |

| Run time | 10.0 min |
|---|---|
| Post time | 0.0 min |
| Flow rate | 1.0 mL/min |
| Injection volume | 5 μL |

TABLE 4-continued

HPLC method for solubility test

| | |
|---|---|
| Detector wavelength | UV at 205 nm |
| Column temperature | 40° C. |
| Sampler temperature | RT |
| Diluent | MeOH |

TABLE 5

HPLC method for purity test

| | |
|---|---|
| HPLC | Agilent 1100 with DAD detector |
| Column | Waters Xbridge Shield RP C18 110A, 150 × 4.6 mm, 5 μm |
| Mobile phase | A: 0.1% TFA in $H_2O$<br>B: 0.1% TFA in acetonitrile |

| Gradient table | Time (min) | % B |
|---|---|---|
| | 0.0 | 20 |
| | 3.0 | 35 |
| | 25.0 | 45 |
| | 35.0 | 95 |
| | 37.0 | 95 |
| | 37.1 | 20 |
| | 40.0 | 20 |

| | |
|---|---|
| Run time | 40.0 min |
| Post time | 0.0 min |
| Flow rate | 1.0 mL/min |
| Injection volume | 5 μL |
| Detector wavelength | UV at 205 nm, reference 500 nm |
| Column temperature | 40° C. |
| Sampler temperature | RT |
| Diluent | Acetonitrile |

SCY-635 free base (Form A) was equilibrated in 96 solvent compositions at 50° C. and subjected to four crystallization techniques: slurry, evaporation, cooling, and precipitation. This automated plate-based screening workflow subjected SCY-635 free base to a total of 384 crystallization experiments.

Crystalline material was only observed from slurry crystallization in heptane, cyclohexane, and water. The form isolated from these experiments was consistent with the provided lot of crystalline SCY-635 free base used for this study (Form A). All other crystallization conditions gave a glass.

The following examples disclosed herein are presented to further describe the invention. However, these examples should not be used to limit the scope of the invention.

A: Examples of Preparation and Identification

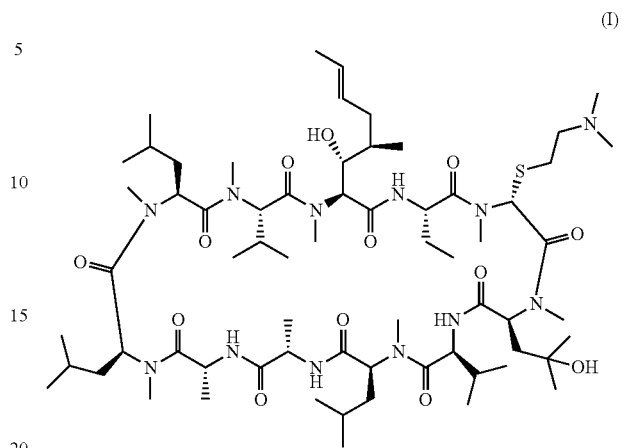

(I)

1. Preparation of the Crystalline Form A of the Compound of Formula (I)

In an inert atmosphere, to a reaction mixture of lithium diisopropylamide in tetrahydrofuran at −35° C., 2.4 g (2.0 mmol) [4'-hydroxy-N-methylleucine]$^4$-cyclosporin A in tetrahydrofuran was slowly charged, the reaction mixture was stirred for 1 hour at −35° C., at which time N,N-dimethylcysteamine was charged while maintaining an internal temperature below −35° C. The reaction was held for 2 hours with stirring at −35° C., at which time glacial acetic acid was added and the reaction was warmed to room temperature. The mixture was diluted with tertiary butyl methyl ether, and washed with saturated sodium bicarbonate solution, and dried over sodium sulphate. Solvent was distilled under vacuum, the residue was purified using silica gel column chromatography, which was first eluted with ethyl acetate/heptane and then with methanol/ethyl acetate, and 560 mg compound of formula (I) (SCY-635) was obtained.

Charge a reactor with 200 mg compound of formula (I), followed by 30 mL acetonitrile. Heat the mixture with agitation to 65° C. and hold for 20 minutes to 1 hour. Filter the mixture through a sintered glass funnel and transfer the filtrate back into the reactor and cool to 10° C. over 1.5-2.0 hours, and hold at 10° C. for a minimum of 15 minutes. Cool the mixture to −10° C. over 1.5-2.0 hours. Filter the mixture and wash the solids with acetonitrile under nitrogen to obtain 153.2 mg the crystalline form A of the compound of formula (I).

2. Identify of the crystalline form A The crystalline form A was analyzed and identified by Empyrean X-ray powder diffraction (XRPD), and the XRPD diffraction spectrogram was shown in FIG. 1, the specific data were shown in table 6. The error margin in 2θ of the characteristic peaks was ±0.2°.

TABLE 6

The XRPD data of the crystalline form A

| Position [° 2θ] | d-Interval [Å] | Relative intensity[%] | Position [° 2θ] | d-Interval [Å] | Relative intensity[%] |
|---|---|---|---|---|---|
| 6.08 | 14.54 | 4.43 | 18.78 | 4.72 | 2.72 |
| 8.66 | 10.21 | 100.00 | 19.38 | 4.58 | 1.56 |
| 9.64 | 9.18 | 8.91 | 20.40 | 4.35 | 7.25 |
| 10.36 | 8.54 | 18.44 | 21.71 | 4.09 | 1.98 |
| 11.20 | 7.90 | 16.22 | 22.04 | 4.03 | 5.20 |

TABLE 6-continued

The XRPD data of the crystalline form A

| Position [° 2θ] | d-Interval [Å] | Relative intensity[%] | Position [° 2θ] | d-Interval [Å] | Relative intensity[%] |
|---|---|---|---|---|---|
| 12.58 | 7.04 | 3.44 | 22.49 | 3.95 | 2.18 |
| 13.00 | 6.81 | 4.68 | 23.20 | 3.83 | 0.98 |
| 13.58 | 6.52 | 1.32 | 23.88 | 3.73 | 0.90 |
| 14.14 | 6.26 | 6.77 | 24.99 | 3.56 | 1.62 |
| 14.90 | 5.95 | 5.56 | 25.82 | 3.45 | 0.75 |
| 15.36 | 5.77 | 2.94 | 26.77 | 3.33 | 1.13 |
| 15.98 | 5.55 | 2.39 | 27.61 | 3.23 | 0.99 |
| 16.71 | 5.30 | 2.65 | 28.43 | 3.14 | 0.93 |
| 17.69 | 5.01 | 2.72 | 29.62 | 3.02 | 0.89 |
| 18.39 | 4.82 | 10.06 | 31.36 | 2.85 | 0.56 |

Figure 2:
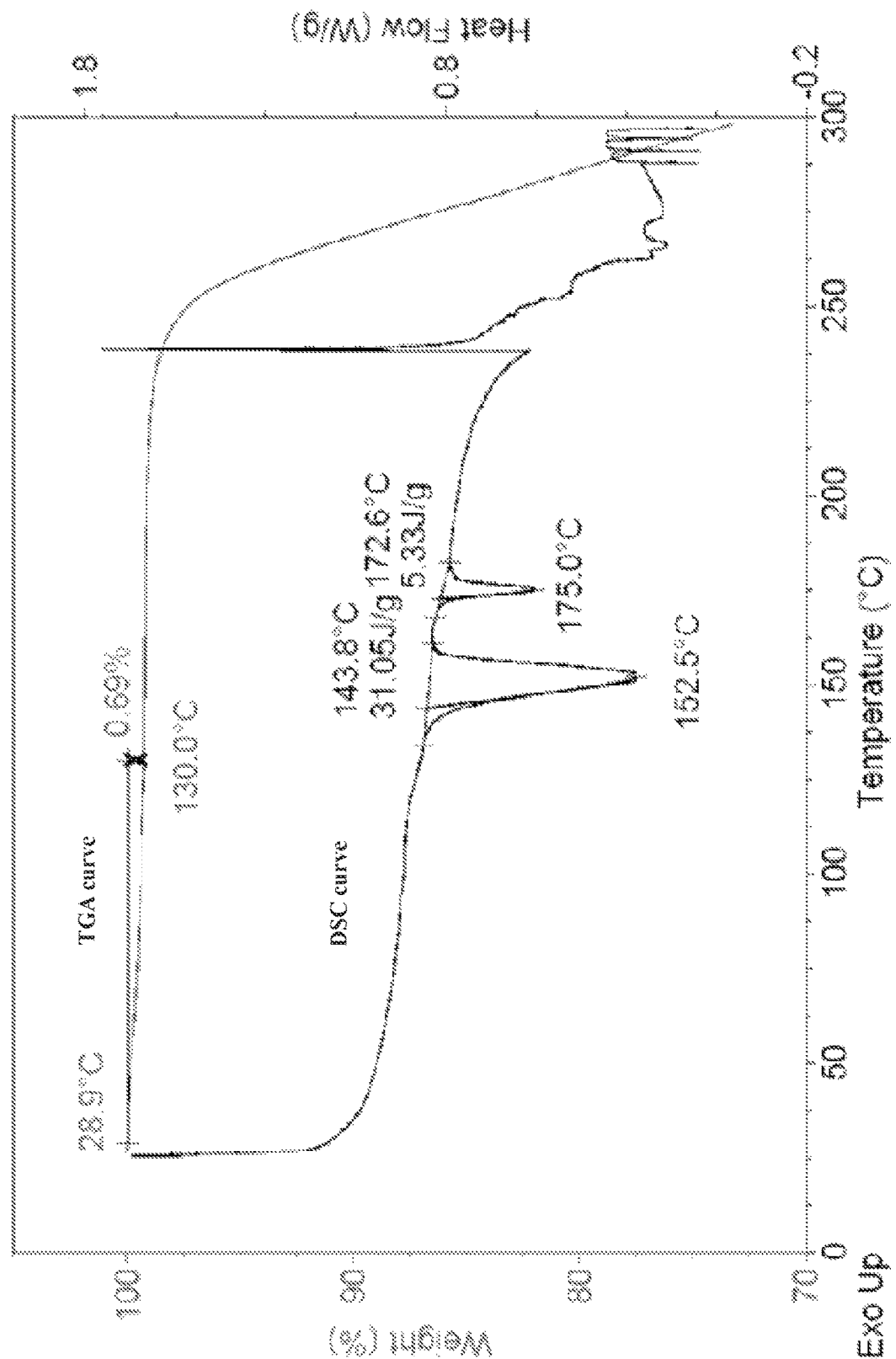
FIG. 2 provides TGA/DSC curves of crystalline form A of the compound having formula (I).
Figure 3:
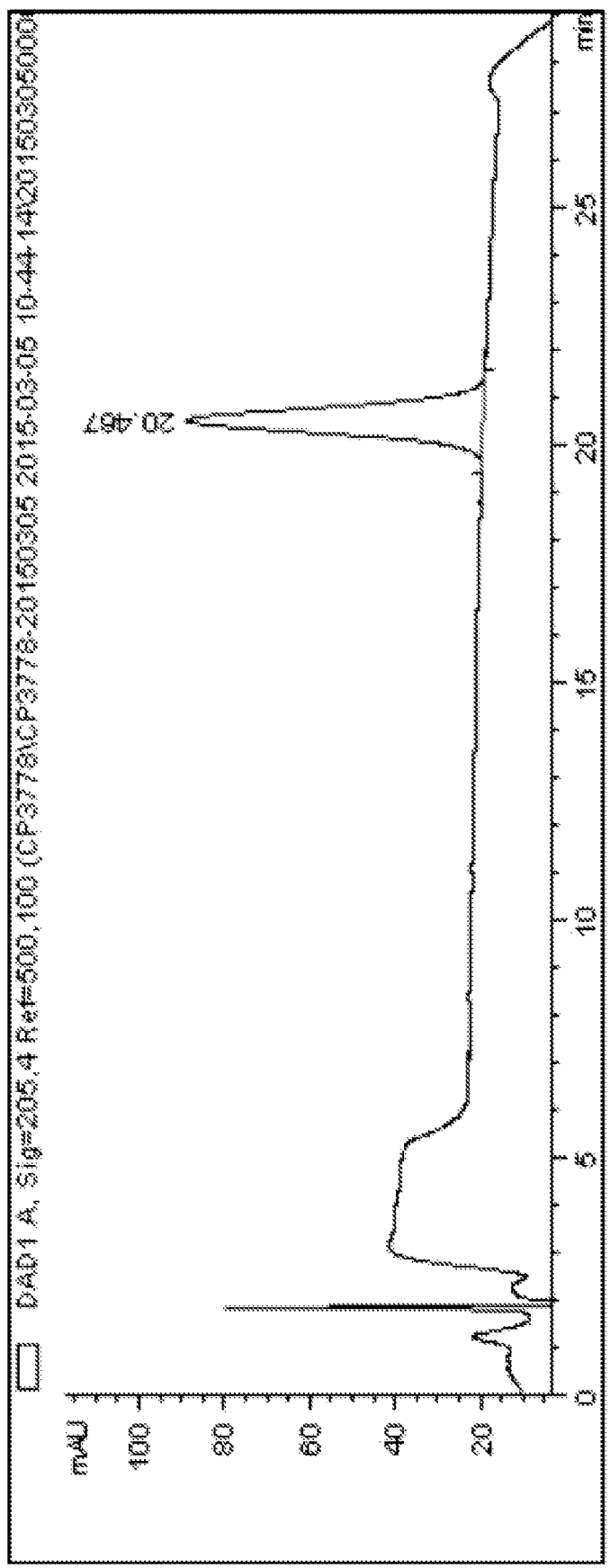
FIG. 3 provides an HPLC chromatograph of crystalline form A of the compound having formula (I).

The TGA/DSC curve was shown in FIG. 2. Negligible weight loss (0.7% up to 130° C.) was observed in TGA. The DSC data showed two endothermic peaks (at 143.8° C. and 172.6° C.) before decomposition, and the error margin of the endothermic peaks was ±3° C. Also, a purity of 100 area % was detected by HPLC and the result was shown in FIG. 3.

Figure 4:
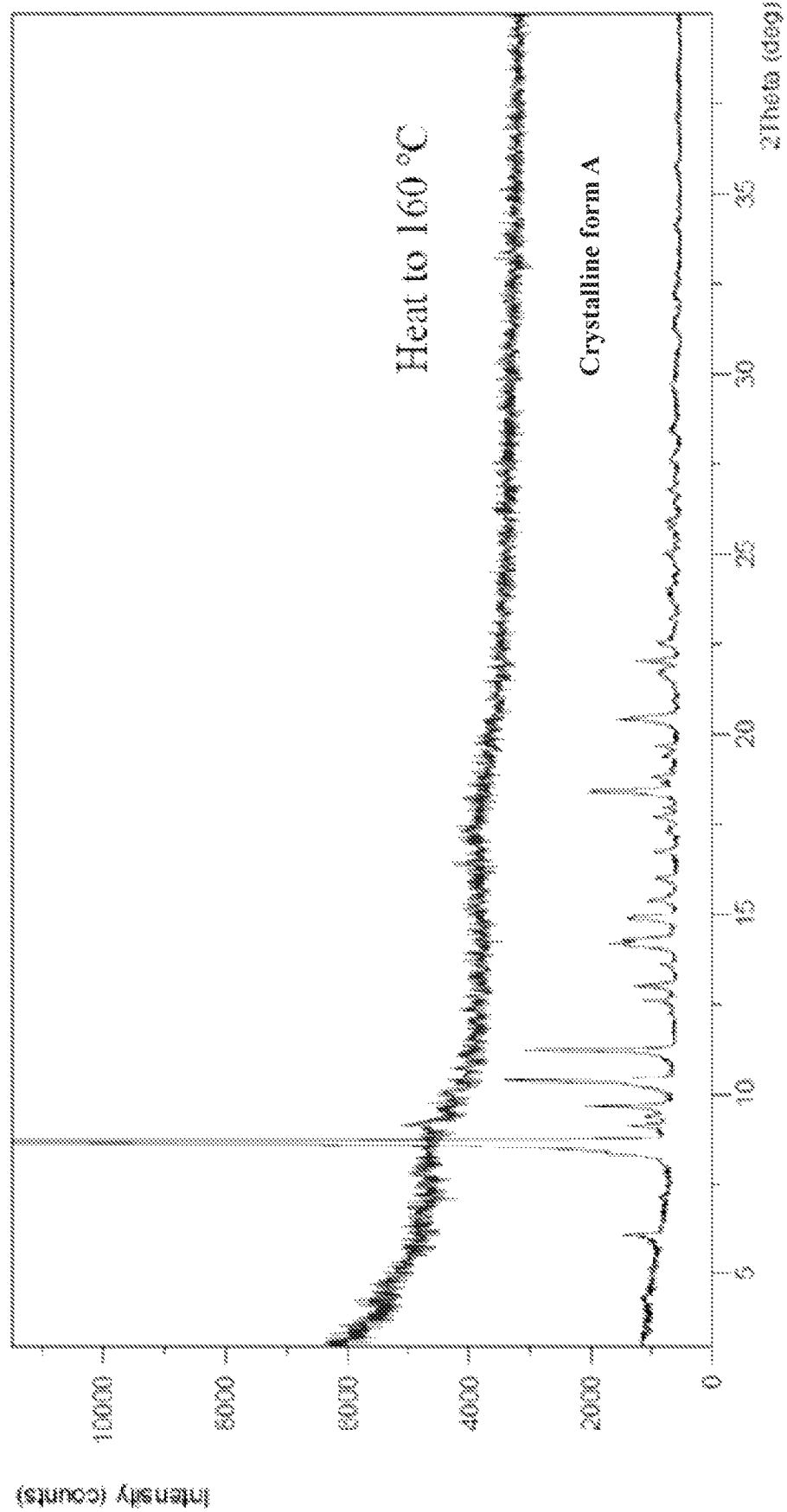
FIG. 4 provides an XRPD pattern of crystalline form A of the compound having formula (I) before and after heating.
Figure 5:
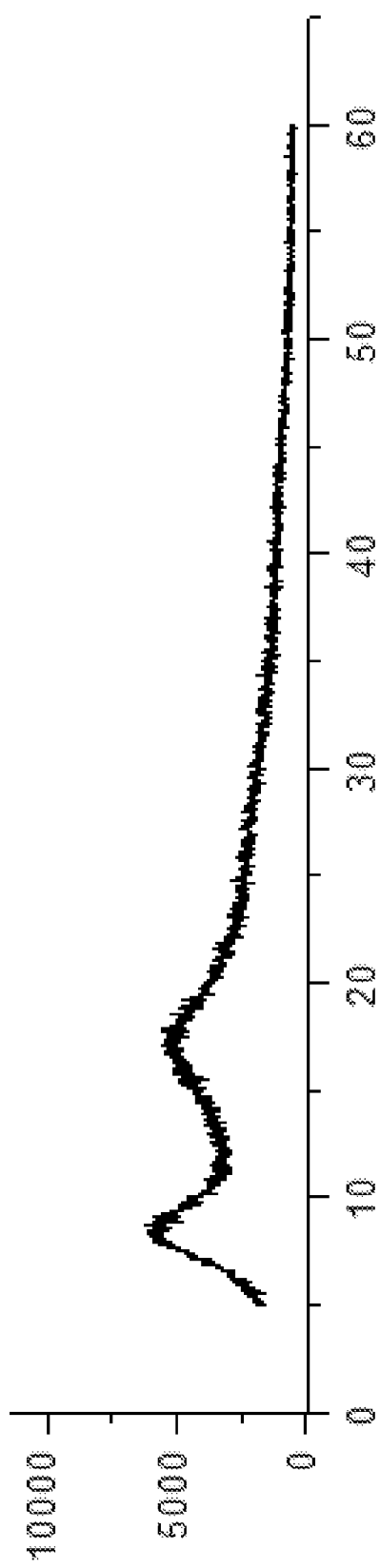
FIG. 5 provides an XRPD pattern of amorphous form of the compound having formula (I).

To figure out if a different crystal form of freebase existed at elevated temperature as shown by two endothermic peaks in DSC curve in FIG. 2, heating experiments of the crystalline form A were conducted and HPLC purity of heated samples was also detected. As the results showed in FIG. 3, FIG. 4 and Table 7, the crystalline form A converted to be amorphous after being heated to 160° C. and decrease of purity from 100% to 97.6% was observed during heating. Also, lower purity at 150° C. compared with 160° C. was speculated to be related to increasing isothermal time. Based on the data above, the second sharp signal was mainly caused by decomposition and no different form was isolated at elevated temperature.

TABLE 7

HPLC purity of heated crystalline form A

| Heating Temperature (° C.) | Appearance | Purity (Area %) |
|---|---|---|
| — | White solid | 100.0 |
| 160, ISO 3 min | Liquated | 97.6 |
| 170, ISO 2 min | Liquated | 94.3 |
| 180, ISO 3 min | Liquated | 88.3 |
| 150, ISO 20 min | Liquated | 95.6 |

—: starting material.
ISO: isothermal.

B: Examples of Properties Test
1. Solubility Test

Solubility of the crystalline form A was estimated in six solvents at RT. Approximately 2 mg of solids were weighed into each 3-mL glass vial, to which each of the solvents in Table 8 was added in increments of 100 μL until the solids dissolved completely or the total volume reached 2 mL.

TABLE 8

Solubility estimation of crystalline form A at RT

| Solvent | Solubility (mg/mL) | Solvent | Solubility (mg/mL) |
|---|---|---|---|
| EtOH | >40.0 | THF | >42.0 |
| Acetone | >40.0 | EtOAc | >42.0 |
| ACN | 10.5 < S < 21.0 | H₂O | <1.1 |

As seen in the data analysis of table 8, the solubility of the crystalline form A is better in EtOH, THF, Acetone and EtOAc.

2. Stability Test

Stability of the crystalline form A was estimated under long term conditions at 25° C./60% RH for at least 24 months and accelerated conditions at 40° C./75% RH for up to 6 months. No significant changes were observed to any of the test parameters including appearance, crystallinity, related substances, water content and assay.

Stability of the crystalline form A was also estimated in water and FaSSIF at room temperature. No solid form changes were observed after 24 hours under both conditions.

Furthermore, it has been found that the crystal form A of the compound having formula (I) has better stability than that of other crystal forms and amorphous forms.

Comparing the stress-testing experimental results of both amorphous form and crystalline form A of SCY-635 free base (under high temperature and photolysis conditions), the total impurity and the major impurities of SCY-635 free base crystalline form A did not increase, its stability was obviously better than that of amorphous form. The specific results are shown in Table 9-10 below.

TABLE 9

Under high temperature (60° C.)

| Days | Purity The amorphous form of SCY-635 free base | Crystal forms The crystalline form A of SCY-635 free base |
|---|---|---|
| 0 | 98.2% | 98.0% |
| 10 | 97.9% | 98.1% |
| 30 | / | 98.0% |
| 50 | 97.7% | / |

Conclusion:

It can be seen from the analysis in Table 9 above that the purity of the amorphous form of SCY-635 free base continued to decrease under the condition of 60° C. in the high temperature test, while the purity of the crystalline form A of SCY-635 free base was not changed, indicating that the stability of the amorphous form was worse than that of the crystal form A.

TABLE 10

Under high photolysis (4500 Lux)

| Days | Purity The amorphous form of SCY-635 free base | Crystal forms The crystalline form A of SCY-635 free base |
|---|---|---|
| 0 | 98.2% | 98.0% |
| 10 | 98.1% | 98.1% |
| 30 | / | 98.0% |
| 50 | 98.0% | / |

Conclusion:

It can be seen from the analysis in Table 10 above that the purity of the amorphous form of SCY-635 free base continued to decrease under the condition of 4500 Lux in the high photolysis test, while the purity of the crystalline form A of SCY-635 free base was not changed, indicating that the stability of the amorphous form was worse than that of the crystal form A.

3. Pharmacokinetic Properties Test (1) Pharmacokinetic Test of the Crystal Form A in Beagle Dogs Pharmacokinetic test of compounds in beagle dogs (weigh: 10-12 kg, male, age: 10-12 months, three members in each oral group and intravenous group) was shown as follows.

Test Method

Beagle dogs received test compounds at a dose of 2.5 mg/kg or 5 mg/kg by oral gavage or at a dose of 1 mg/kg or 2 mg/kg by intravenous injection.

Blood samples of vein were taken at 0.083, 0.25, 0.5, 1, 2, 4, 6, 8 and 24 hours after the administration, and collected in anticoagulation tube with EDTA-$K_2$. The test compounds were extracted from plasma samples by liquid-liquid extraction. Then quantitative analysis was performed on a triple-quadrupole tandem mass spectrometer using multiple reaction monitoring (MRM). Pharmacokinetic parameters were calculated using a noncompartmental method by WinNonLin 6.3 software.

Conclusion: the pharmacokinetic data show that the crystal form A of the compound having formula (I) has better pharmacokinetic properties in vivo of beagle dogs than that of other crystal forms and amorphous forms, and has a good application prospect in anti-HCV virus.

(2) Pharmacokinetic Test in Mice

Pharmacokinetic test of compounds in mice (weigh: 20-25 g, male, age: 45-60 days, three members in each oral group and intravenous group) was shown as follows.

Test Method

ICR mice received test compounds at a dose of 10 mg/kg by oral gavage or at a dose of 2 mg/kg or 10 mg/kg by tail intravenous injection. Blood samples of orbital vein were taken at 0.083, 0.25, 0.5, 1, 2, 4, 6, 8 and 24 hours after the administration, and collected in anticoagulation tube with EDTA-$K_2$. The test compounds were extracted from plasma samples by liquid-liquid extraction. Then quantitative analysis was performed on a triple-quadrupole tandem mass spectrometer using multiple reaction monitoring (MRM). Pharmacokinetic parameters were calculated using a non-compartmental method by WinNonLin 6.1 software.

Conclusion: the pharmacokinetic data show that the crystal form A of the compound having formula (I) has better pharmacokinetic properties in vivo of mice than that of other crystal forms and amorphous forms, and has a good application prospect in anti-HCV virus.

(3) Pharmacokinetic Test in SD Rat

Pharmacokinetic test of compounds of the invention in SD rats (weigh: 200-250 g, male, age: 2-3 months, three members in each oral group and intravenous group) was shown as follows.

Test Method

Rats received test crystal form A at a dose of 2.5 mg/kg or 5 mg/kg by oral gavage or at a dose of 1 mg/kg by intravenous injection.

Blood samples of vein were taken at 0.083, 0.25, 0.5, 1, 2, 5, 7 and 24 hours after the administration, and collected in anticoagulation tube with EDTA-$K_2$. The test compounds were extracted from plasma samples by liquid-liquid extraction. Then quantitative analysis was performed on a triple-quadrupole tandem mass spectrometer using multiple reaction monitoring (MRM). Pharmacokinetic parameters were calculated using a noncompartmental method by WinNonLin 6.3 software.

Conclusion: the pharmacokinetic data show that the crystal form A of the compound having formula (I) has better pharmacokinetic properties in vivo of SD rats than that of other crystal forms and amorphous forms, and has a good application prospect in anti-HCV virus.

4. SCY-635 Free Base Crystalline Form A Bioavailability, Pharmacokinetics and In-Vitro/In-Vivo Activity Anti-HCV Activity of SCY-635 in the Replicon Assay The purpose of this study was to assess the potential anti-HCV activity of SCY-635 (free base crystalline form A) in the well-characterized genotype-1 replicon. The first reproducible HCV replication system in cell culture (Huh7 hepatoma cell line) was reported in 1999 (Lohmann et al., 1999). The assay utilizes bi-cistronic subgenomic viral RNAs, or replicons, that encode nonstructural proteins and have the cis RNA elements required for autonomous replication. Replicons are self-replicating RNA molecules that contain all of the nucleotide sequences required for HCV replication, transcription, and translation, but are not infectious.

SCY-635 (free base crystalline form A) was studied in the HCV Replicon assay to evaluate its ability to inhibit HCV genomic replication. It was tested for activity against HCV using the methods adapted from those described by Krieger et al., (2001) and Pietschmann et al., (2002), and using HCV RNA constructs as described in U.S. Pat. No. 6,630,343.

Methods

SCY-635 (free base crystalline form A) was examined in the human hepatoma cell line ET (lub ubi neo/ET), an HCV RNA replicon containing a stable luciferase (LUC) reporter. The HCV RNA replicon ET contains the 5' end of HCV (with the HCV Internal Ribosome Entry Site (IRES) and the first few amino acids of the HCV core protein) which drives the production of a firefly luciferase (LUC), ubiquitin, and neomycin phosphotransferase (NeoR) fusion protein. Ubiquitin cleavage releases the LUC and NeoR proteins. The EMCV IRES element controls the translation of the HCV structural proteins NS3-NS5. The NS3 protein cleaves the HCV polyprotein to release the mature NS3, NS4A, NS4B, NS5A and NS5B proteins that are required for HCV replication. The 3' end of the replicon contains the authentic 3' NTR of HCV. The activity of the LUC reporter is directly proportional to HCV replication levels and positive-control antiviral compounds produce a reproducible antiviral response using the LUC endpoint.

The compound was dissolved in dimethyl sulfoxide (DMSO) and diluted into culture medium at five half-log concentrations, ranging from either 0.02 to 2.0 µM (for SCY-635), or 0.2 to 20 µM (for CsA). Subconfluent cultures of the ET line were plated out into 96 well plates dedicated for the analysis of cell numbers (cytotoxicity) or antiviral activity and the next day the compounds were added to the appropriate wells. The cells were processed 72 hours later when the cells were still subconfluent. Antiviral activity was expressed as $EC_{50}$ and $EC_{90}$, the effective concentrations of compound that reduced viral replication by 50% and 90%, respectively. $EC_{50}$ and $EC_{90}$ values were derived from HCV RNA levels assessed as HCV RNA replicon derived LUC activity. Cytotoxicity was expressed as $IC_{50}$ and $IC_{90}$, the concentration of compound that inhibited cell viability by 50% and 90%, respectively. $IC_{50}$ and $IC_{90}$ values were calculated using a colorimetric assay as an indication of cell numbers and cytotoxicity. The activity of the LUC reporter is directly proportional to HCV RNA levels in the human cell line. The HCV-replicon assay was validated in parallel experiments using interferon-alpha-2b as a positive control.

RESULTS AND CONCLUSION

When tested in the replicon assay, SCY-635 free base crystalline form A exhibits potent anti-HCV activity in the absence of cell cytotoxicity. It exhibits $EC_{50}$ values of 100 nM (132 ng/mL) and 170 nM (225 ng/mL) against con 1b derived bi-cistronic and full length replicons, respectively. The corresponding $EC_{90}$ values for SCY-635 free base crystalline form A in the bi-cistronic and full length replicons are 350 nM (463 ng/mL) and 690 nM (912 ng/mL), respectively. When tested in the H77 replicon (genotype 1a), SCY-635 free base crystalline form A exhibits $EC_{50}$ and $EC_{90}$ values of 150 nM (198 ng/mL) and 1380 nM (1,824 ng/mL), respectively.

SCY-635 free base crystalline form A is orally bioavailable in mice, rats, dogs, monkeys and humans. Pharmacokinetic studies have shown that SCY-635 free base crystalline form A was absorbed into the systemic circulation following oral administration. Differential penetration into whole blood and plasma compartments was observed at all dose levels with the majority of the drug being associated with the whole blood fraction. It exhibits dose-dependent pharmacokinetic behavior that was similar in normal healthy volunteers and subjects with chronic HCV infection.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

What is claimed is:

1. The crystalline form A of the compound having formula (I):

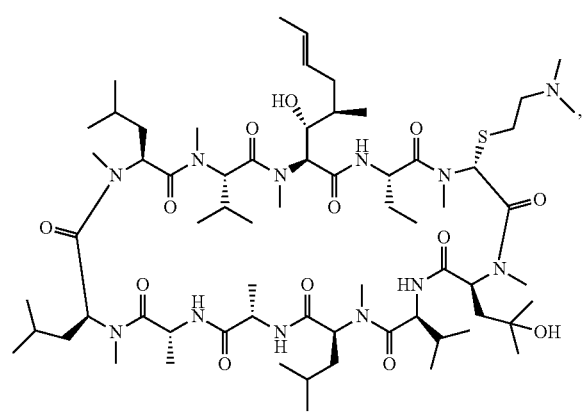

wherein the crystalline form A exhibits the following characteristic X-ray powder diffraction peaks expressed in degrees 2θ at 8.66±0.2°, 9.64±0.2°, 10.36±0.2°, 11.20±0.2°, 18.39±0.2°.

2. The crystalline form A of claim 1, wherein the crystalline form A exhibits the following characteristic X-ray powder diffraction peaks expressed in degrees 2θ at 6.08±0.2°, 8.66±0.2°, 9.64±0.2°, 10.36±0.2°, 11.20±0.2°, 13.00±0.2°, 14.14±0.2°, 14.90±0.2°, 18.39±0.2°, 20.40±0.2°, 22.04±0.2°.

3. The crystalline form A of claim 1, wherein the crystalline form A exhibits the following characteristic X-ray powder diffraction peaks expressed in degrees 2θ at 6.08±0.2°, 8.66±0.2°, 9.64±0.2°, 10.36±0.2°, 11.20±0.2°, 12.58±0.2°, 13.00±0.2°, 13.58±0.2°, 14.14±0.2°, 14.90±0.2°, 15.36±0.2°, 15.98±0.2°, 16.71±0.2°, 17.69±0.2°, 18.39±0.2°, 18.78±0.2°, 19.38±0.2°, 20.40±0.2°, 21.71±0.2°, 22.04±0.2°, 22.49±0.2°, 23.20±0.2°, 23.88±0.2°, 24.99±0.2°, 25.82±0.2°, 26.77±0.2°, 27.61±0.2°, 28.43±0.2°, 29.62±0.2°, 31.36±0.2°.

4. The crystalline form A of claim 1, wherein the crystalline form A has a differential scanning calorimetry thermogram comprising an endothermic peak at 143.8° C.±3° C., 172.6° C.±3° C.

5. A pharmaceutical composition comprising the crystalline form A of claim 1, wherein the pharmaceutical composition further comprises a pharmaceutically acceptable excipient, or a combination of the excipients.

6. The pharmaceutical composition according to claim 5 further comprising other anti-HCV drug.

7. The pharmaceutical composition according to claim 6, wherein the other anti-HCV drug is Ledipasvir/sofosbuvir, Sofosbuvir, Ribavirin, Peginterferon alfa-2a or Daclatasvir.

8. A method of preventing, treating or lessening a disorder or disease caused by a virus infection in a patient comprising administering to the patient a therapeutically effective amount of the crystalline form A according to claim 1.

9. The method according to claim 8, wherein the virus infection is hepatitis C infection.

* * * * *